US010888050B2

(12) United States Patent
Erickson

(10) Patent No.: US 10,888,050 B2
(45) Date of Patent: *Jan. 12, 2021

(54) AIR POLLUTION ABATEMENT AND CROP GROWTH STIMULATION TECHNOLOGY

(71) Applicant: The Agricultural Gas Company, Inc., Petaluma, CA (US)

(72) Inventor: Stewart E. Erickson, Petaluma, CA (US)

(73) Assignee: The Agricultural Gas Co., Petaluma, CA (US)

(*) Notice: Subject to any disclaimer, the term of this patent is extended or adjusted under 35 U.S.C. 154(b) by 48 days.

This patent is subject to a terminal disclaimer.

(21) Appl. No.: 16/199,968

(22) Filed: Nov. 26, 2018

(65) Prior Publication Data

US 2020/0008368 A1    Jan. 9, 2020

Related U.S. Application Data

(63) Continuation-in-part of application No. 16/026,390, filed on Jul. 3, 2018.

(51) Int. Cl.
| | | |
|---|---|---|
| *A61L 9/015* | (2006.01) | |
| *A01G 7/00* | (2006.01) | |
| *A01G 13/02* | (2006.01) | |

(52) U.S. Cl.
CPC .......... *A01G 13/0206* (2013.01); *A61L 9/015* (2013.01); *A61L 2209/111* (2013.01); *A61L 2209/14* (2013.01); *A61L 2209/213* (2013.01)

(58) Field of Classification Search
CPC .. A01G 7/00; A01G 13/00; A61L 2/20; A61L 9/015
See application file for complete search history.

(56) References Cited

U.S. PATENT DOCUMENTS

| | | | | |
|---|---|---|---|---|
| 4,744,951 | A | * | 5/1988 | Cummings ............... A61L 2/20 422/28 |
| 2008/0264140 | A1 | * | 10/2008 | Hill .................... G01N 33/0006 73/1.03 |
| 2016/0257055 | A1 | * | 9/2016 | Hayakawa ................ A61L 2/06 |

* cited by examiner

*Primary Examiner* — Monica L Barlow
(74) *Attorney, Agent, or Firm* — Joel Skinner; Skinner & Associates

(57) ABSTRACT

A system and method of abating air pollution and stimulating crop growth. A reagent is introduced to a crop canopy to neutralize air pollutants within said canopy, wherein the reagent induces an oxidation-reduction chemical reaction with the air pollution present throughout the acreage of crops, and by means of the reaction effectually neutralizes the harmful effects of the air pollutants on the crops. The reagent is diluted using a venturi valve or other means. The flow rate of said reagent is regulated using an electronic control unit, based on data collected from at least one type of sensor in the canopy that is in communication with the control unit.

15 Claims, 4 Drawing Sheets

Figure 1:
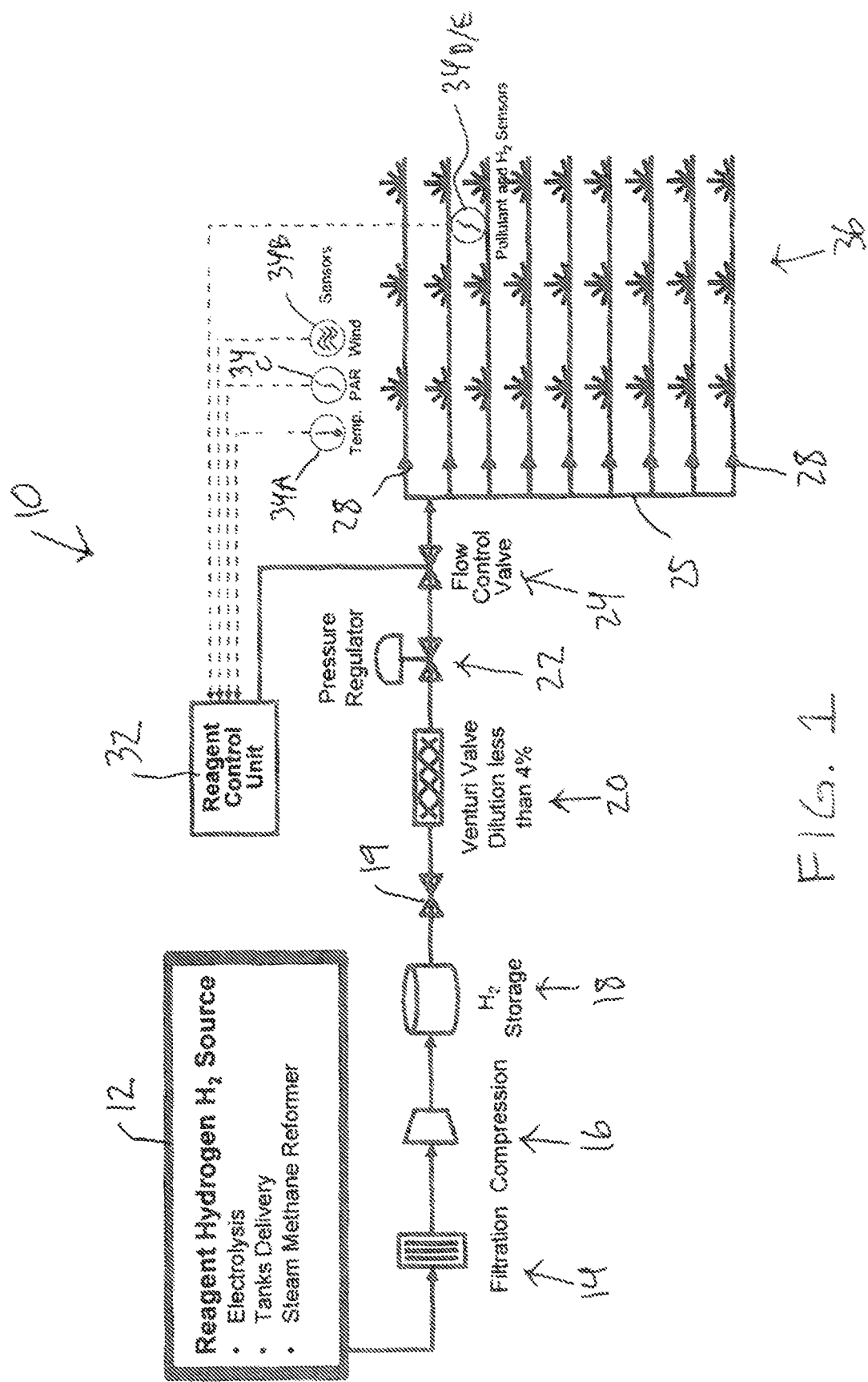

| Reaction Components | Temperature °K | Temperature °C | Pressure mmHG | Time Hours |
|---|---|---|---|---|
| $CH_4 + 4/3\ O_3$ | 195-294 | -78 - +21 | 778 - 910 | 1 - 22 |
| $O_3 + NO \rightarrow O_2 + NO_2$ | STP | STP | STP | --- |
| $NH_3 + \frac{1}{2} O_3$ | 273 | 0 | 765 | --- |
| $CO + 1/3\ O_3$ | 195 | -78 | 752 | --- |
| $SO_2 + 1/3\ O_3$ | 273 | 0 | 760 | 12 |
| $PH_3 + 4/3\ O_3$ | 195 | -78 | 760 | --- |

FIG. 6

| Chemical Reaction | Temp (K) | A | n | Ea (kJ/mole) | k (298 K) | Order |
|---|---|---|---|---|---|---|
| $O_3 + N \rightarrow O_2 + NO$ | 298 | <2.01E-16 | --- | --- | <2.01E-16 | 2 |
| $O_3 + NO \rightarrow O_2 + NO_2$ | 298 | 1.80E-14 | --- | --- | 1.80E-14 | 2 |
| $O_3 + NO_2 \rightarrow O_2 + NO_3$ | 298 | 3.50E-17 | --- | --- | 3.50E-17 | 2 |
| $O_3 + O \cdot \rightarrow O_2 + O_2$ | 298 | 8.00E-12 | --- | 17.13 | 8.00E-15 | 2 |
| $O_3 + H \cdot \rightarrow \cdot OH + O_2$ | 200-300 | 1.40E-10 | --- | 3.91 | 2.89E-11 | 2 |
| $CO + O_3 \rightarrow CO_2 + O_2$ | 296 | <4.00E-25 | --- | --- | --- | 2 |
| $CH_4 + O_3 \rightarrow Products$ | 298 | <1.20E-21 | --- | --- | 1.20E-21 | 3 |
| $SO_2 + O_3 \rightarrow SO_3 + O_2$ | 200-300 | 3.01E-12 | --- | 58.20 | 1.89E-22 | 2 |

FIG. 7

AIR POLLUTION ABATEMENT AND CROP GROWTH STIMULATION TECHNOLOGY

CROSS-REFERENCE TO RELATED APPLICATIONS, IF ANY

This application is a Continuation-In-Part of pending U.S. patent application Ser. No. 16/026,390, filed Jul. 3, 2018, which claims the benefit under 35 U.S.C. § 119(e) of U.S. Provisional Patent Application Ser. No. 62/528,189, filed Jul. 3, 2017, which is hereby incorporated by reference.

37 C.F.R. § 1.71(e) AUTHORIZATION

A portion of the disclosure of this patent document contains material which is subject to copyright protection. The copyright owner has no objection to the facsimile reproduction by anyone of the patent document or the patent disclosure, as it appears in the US Patent and Trademark Office patent file or records, but otherwise reserves all copyright rights whatsoever.

STATEMENT REGARDING FEDERALLY SPONSORED RESEARCH OR DEVELOPMENT

Not applicable.

BACKGROUND OF THE INVENTION

1. Field of the Invention

The present invention relates, generally, to agricultural and environmental systems, apparatus and methods. Particularly, the invention relates to a method of abating air pollution and stimulating crop growth.

2. Background Information

It may be hard to imagine that pollution could be invisible, but ozone is. The most widespread pollutant in the U.S. is also one of the most dangerous. Scientists have studied the effects of ozone on health for decades. Hundreds of research studies have confirmed that ozone harms people at levels currently found in the United States.

Ozone is also harmful to the plants we grow for nutrition. According to the United States Department of Agriculture, ground-level ozone causes more damage to plants than all other air pollutants combined. As a strong oxidant, ozone causes several types of symptoms including chlorosis and necrosis. Furthermore, controlled studies in open-top field chambers have repeatedly verified that flecking, stippling, bronzing and reddening on plant leaves are classical responses to ambient levels of ozone. In terms of crop yield loss caused by ozone, similar open-top studies conducted by the National Crop Loss Assessment Network showed between 35 and 45 percent yield loss among dicot species when exposed to ambient ozone at 100 parts per billion. The present invention hopes to ameliorate this situation.

What is Ozone?

Ozone (O3) is a gas molecule composed of three oxygen atoms. Often called "smog," ozone is harmful to breathe. Ozone aggressively attacks lung tissue by reacting chemically with it.

The ozone layer found high in the upper atmosphere (the stratosphere) shields us from much of the sun's ultraviolet radiation. However, ozone air pollution at ground level where we can breathe it (in the troposphere) causes serious health problems.

Where does Ozone Come From?

Ozone develops in the atmosphere from gases that come out of tailpipes, smokestacks and many other sources. When these gases come in contact with sunlight, they react and form ozone smog.

The essential raw ingredients for ozone come from nitrogen oxides (NOx), hydrocarbons, also called volatile organic compounds (VOCs) and carbon monoxide (CO). They are produced primarily when fossil fuels like gasoline, oil or coal are burned or when some chemicals, like solvents, evaporate. NOx is emitted from power plants, motor vehicles and other sources of high-heat combustion. VOCs are emitted from motor vehicles, chemical plants, refineries, factories, gas stations, paint and other sources. CO is also primarily emitted from motor vehicles.

If the ingredients are present under the right conditions, they react to form ozone. And because the reaction takes place in the atmosphere, the ozone often shows up downwind of the sources of the original gases. In addition, winds can carry ozone far from where it began.

Hydrogen as a Solution

For over 40 years, industry has used hydrogen in vast quantities as an industrial chemical and fuel for space exploration. During that time, industry has developed an infrastructure to produce, store, transport and utilize hydrogen safely.

Hydrogen is no more dangerous than other flammable fuels, including gasoline and natural gas. In fact, some of hydrogen's differences actually provide safety benefits compared to gasoline or other fuels. However, all flammable fuels must be handled responsibly.

Like gasoline and natural gas, hydrogen is flammable and can behave dangerously under specific conditions. Hydrogen can be handled safely when simple guidelines are observed and the user has an understanding of its behavior. The following lists some of the most notable differences:

1) Hydrogen is lighter than air and diffuses rapidly. Hydrogen has a rapid diffusivity (3.8 times faster than natural gas), which means that when released, it dilutes quickly into a non-flammable concentration. Hydrogen rises 2 times faster than helium and 6 times faster than natural gas at a speed of almost 45 mph (20 m/s). Therefore, unless a roof, a poorly ventilated room or some other structure contains the rising gas, the laws of physics prevent hydrogen from lingering near a leak (or near people using hydrogen-fueled equipment). Simply stated, to become a fire hazard, hydrogen must first be confined—but as the lightest element in the universe, confining hydrogen is very difficult. Industry takes these properties into account when designing structures where hydrogen will be used. The designs help hydrogen escape up and away from the user in case of an unexpected release.

2) Hydrogen is odorless, colorless and tasteless, so most human senses won't help to detect a leak. However, given hydrogen's tendency to rise quickly, a hydrogen leak indoors would briefly collect on the ceiling and eventually move towards the corners and away from where any nose might detect it. For that and other reasons, industry often uses hydrogen sensors to help detect hydrogen leaks and has maintained a high safety record using them for decades. By comparison, natural gas is also odorless, colorless and tasteless, but industry adds a sulfur-containing odorant, called mercaptan, to make it detectable by people. Currently, all known odorants contaminate fuel cells (a popular application for hydrogen). Researchers are investigating other methods that might be used for hydrogen detection: tracers, new odorant technology, advanced sensors and others.

3) Hydrogen flames have low radiant heat. Hydrogen combustion primarily produces heat and water. Due to the absence of carbon and the presence of heat-absorbing water vapor created when hydrogen burns, a hydrogen fire has significantly less radiant heat compared to a hydrocarbon fire. Since the flame emits low levels of heat near the flame (the flame itself is just as hot), the risk of secondary fires is lower.

4) Like any flammable fuel, hydrogen can combust. But hydrogen's buoyancy, diffusivity and small molecular size make it difficult to contain and create a combustible situation. In order for a hydrogen fire to occur, an adequate concentration of hydrogen, the presence of an ignition source and the right amount of oxidizer (like oxygen) must be present at the same time. Hydrogen has a wide flammability range (4-74% in air).

Meanwhile, plants require hydrogen to form carbohydrates and sugars. Plants currently assemble all of their hydrogen requirements by splitting water molecules $H_2O$ in the photosynthetic process in the leaves of plants when exposed to sunlight. So, hydrogen is already present in the leaves and is a molecule synthesized for plant growth.

Existing technology in this field is believed to have significant limitations and shortcomings. For this reason and those described above, a need exists for the present invention.

All US patents and patent applications, and all other published documents mentioned anywhere in this application are incorporated by reference in their entirety.

BRIEF SUMMARY OF THE INVENTION

The invention provides systems and methods which are practical, reliable and efficient, and which are believed to fulfill the need and to constitute an improvement over the background technology.

The invention has at least the following aspects:

1. A system including a compression source, reagent source, and grid of tubes in a field of crops, to prescriptively distribute an air pollution negating reagent into the atmosphere immersing a field of crops.
2. Introduction of a reagent that is non-toxic to plants, over a large acreage, wherein said reagent induces an oxidation-reduction chemical reaction with the air pollution present throughout the acreage of crops, by means of the reaction effectually neutralizing the harmful effects of the air pollutants notably $O_3$ and $NO_x$ on the crops.
3. Said reagent is hydrogen $H_2$ gas that is delivered in the distribution grid at a diluted ratio not to exceed the flammability point of 4% $H_2$ concentration in ambient air.
4. The delivering actuation and rate of delivery of the reagent is determined by the level of air pollution, so that the chemical reaction neutralizing effect envelopes, but does not vastly exceed the space occupied by the crops' foliar canopy.
5. Hydrogen delivery in aerial application as an airborne fertilizer to stimulate carbohydrate formation in the leaves of plants.
6. Source of reagent is a compressed tank.
7. Source of reagent is a steam methane reformer.
8. Source of reagent is electrolysis.

The aspects, features, advantages, benefits and objects of the invention will become clear to those skilled in the art by reference to the following description, claims and drawings.

BRIEF DESCRIPTION OF THE SEVERAL VIEWS OF THE DRAWING

FIG. 1 illustrates an embodiment of the present invention.

FIG. 2 is a graph depicting ozone concentration levels by altitude.

FIG. 3 is a diagram depicting arrangements of oxygen atoms.

FIG. 4 is a table listing the physical properties of ozone.

FIG. 5 is a table depicting the resonance structures of ozone and its half-life with respect to temperature.

FIG. 6 is a table listing candidates for reaction with ozone which are in gaseous state.

FIG. 7 is a table listing kinetic information on the gaseous candidates.

DETAILED DESCRIPTION

The present invention provides a Crop Growth Enhancement Method using a Reagent to Neutralize Air Pollutants.

FIG. 1 shows the pollution abatement system 10 of the present invention. O3 ozone, nitric oxide and nitrogen dioxide are common oxidation agents associated with air pollution and are very deleterious to human health and plant/crop health and productivity. The system 10 introduces a reagent to the crop canopy to neutralize ozone, nitric oxide and nitrogen dioxide from the canopy through oxidation-reduction chemical reactions. All parts of the device are shown in the following Parts List:

| PART NO. | PART NAME/DESCRIPTION |
|---|---|
| 10 | Overall System |
| 12 | reagent source |
| 14 | filtration device |
| 16 | compressor |
| 18 | hydrogen storage |
| 19 | valve |
| 20 | venturi valve |
| 22 | pressure regulator |
| 24 | flow control valve |
| 25 | manifold |
| 26 | release point |
| 28 | emitter |
| 30 | emitter array |
| 32 | electronic controller unit |
| 34 | data sensors A-D |
| 36 | plant group |
| 38 | plant canopy |

A basic embodiment includes a hydrogen source 12, a compressor 16, and interconnecting lines and manifolds to distribute the hydrogen 12 to a group of plants 30, via one or more emitters 28. Where the hydrogen is deployed at multiple locations among the group of plants 36, a manifold 25 may be connected between the output of the compressor 16 and an emitter array 30. The type of manifold 25 used may be of the layflat design typically employed in agricultural applications. The hydrogen source 12 may be a tank, either fixed or semi-portable. Alternatively, it may be through electrolysis or steam reforming methods. The plant group 36 includes a plurality of individual plants, which may be disposed in a greenhouse, hoop house, or the like.

Alternatively, the group 36 may be disposed outside in a field, orchard, vineyard or the like.

In a more preferred embodiment, one or more sensors 34 are preferably connected to a controller 32 to prescriptively add hydrogen gas 12 based on the concentration of pollutants detected in the atmosphere immediately surrounding the plant group 36. Hydrogen sources include electrolysis of water or other substance containing hydrogen, steam reforming from methane or another hydrocarbon, and the like.

Still referring to FIG. 1, a most preferred embodiment of the system 10 includes a hydrogen source 12 input, preferably to a filter 14. The output of the filter 14 is connected to the compressor 16. The compressor 16 output is connected to a hydrogen storage container 18. A valve 19 is interconnected between the output of the hydrogen storage 18 and a Venturi valve 20. The output of the Venturi valve 20 is connected to a pressure regulator 22. The pressure regulator 22 is connected to a flow control valve 24, which controls flow to the emitter array 30. The flow control valve 24 is communicatively connected to the electronic controller 32. The sensors 34 are also communicatively connected to the controller 32. The sensors 34 preferably include a hydrogen concentration sensor 34$x$ and a one or more pollutant concentration sensors 34$y$, measuring concentrations of ozone, nitrous oxide, and/or nitrogen dioxide, disposed within the plant group 36, preferably closely proximate to the plant canopy 38. Sensors' 34 positions may be adjusted to remain close to the plant canopy 38 as the plants grow vertically. The sensors may also include a temperature sensor(s) 34$z$, a PAR sensor(s) 34$q$, and a wind sensor(s) 34$w$.

The present invention relates to introducing a reducing chemical reagent and oxygen molecule acceptor of an oxidation-reduction reaction. In the case of Hydrogen gas being the acceptor, the reaction is either $O_3+H_2 \rightarrow O_2+H_2O$ for ozone as oxidizing agent, or $2NO+2H_2 \rightarrow N_2+2H_2O$ for nitric oxide as oxidizing agent, or $2NO_2+4H_2 \rightarrow N_2+4H_2O$ for nitrogen dioxide as oxidizing agent.

Because hydrogen gas is a very active reducing agent with the oxidizing agent $O_2$, hydrogen is highly explosive in air. However, in prescriptive amounts where the concentration of the $H_2$ gas in ambient air is less than 4% (below combustion point), the hydrogen is not flammable or explosive. The flammability limits, based on the volume percent of hydrogen in air at 14.7 psia (1 atm, 101 kPa), are 4.0 and 75.0. The limits of detonability of hydrogen in air are 18.3 to 59 percent by volume. The flow rate of the distribution emitter array 30 is set so that just enough hydrogen is introduced so as to maintain less than 4% ambient air concentration, which is below the point of combustion of the hydrogen.

The present invention is a system and method of using a hydrogen source, a compressor, and manifolds to distribute $H_2$ or other $O_3$ neutralizing agent based upon pollution levels. Sensors 34 are connected to a controller 32 to prescriptively add $H_2$ at a rate sufficient to neutralize the $O_3$ levels present in the leafy canopy 38 of the crops. The hydrogen diffuses rapidly from the emitters and is lighter than air so rises up through the plant canopy 38 into the surrounding air. The systems seek to achieve a special prescription of 0.097 ppm which is the ozone level in Fresno, Calif., one of the most polluted regions of the United States. Similarly high pollutant levels are present through San Joaquin Valley, the region which produces most of the fruits, nuts and vegetables consumed in the US.

In the first step of the method, hydrogen is acquired from one of several sources, including: electrolysis of water or other hydrogen-containing substance, delivered in pure form in tanks, harvested from methane or other hydrocarbon using steam reforming, or another source.

The hydrogen gas is filtered of impurities in the second step of the method using a hydrogen purification device 14. This step may not be necessary in the case of tank delivered hydrogen but is necessary for hydrogen sourced from hydrocarbons such as methane. Possible hydrogen purification methods include palladium membranes, dense thin-metal membrane purifiers, pressure swing adsorption, catalytic recombination, or an electrochemical purification system, the latter of which can have the added benefit of compressing the hydrogen simultaneously.

The third step is the compression of the purified hydrogen for ease of storage using a compressor 16. Possible methods for compressing hydrogen include: reciprocating piston compressors, ionic liquid piston compressors, hydride compressors, piston-metal diaphragm compressors, guided rotor compressors, and the highly efficient electrochemical hydrogen compressor. The compressed hydrogen can then be stored in containers until needed or be directed into the system immediately.

In the fourth step, the hydrogen is diluted with ambient air or other gaseous media so that the hydrogen component is equal to, or less than, 4% of the total gaseous mixture, which will prevent the hydrogen from sustaining a spontaneous combustive reaction, should an ignition source be present. This dilution is preferably accomplished using a venturi valve 20. The venturi valve 20 dilution process utilizes the Venturi effect, whereby a constriction of the diameter for a short stretch of the valve causes a drop in pressure. The low-pressure area creates suction which draws in a diluent such as oxygen which mixes with the hydrogen gas stream.

During the fifth step of the method the pressure is modified as needed by a pressure regulator 22, and the flow rate is regulated by a flow control valve 24. The regulator 22 can be a single-stage or double-stage regulator. The flow control valve 24 is connected via a manifold 25, preferably a layflat manifold to the array of piping which distributes gas throughout the crop field.

The layflat type of manifold is commonly used by growers to deliver water. Using a layflat manifold to deliver gas therefore has the advantages that those managing the field are familiar with its service and maintenance. The flow rate of the valve 24 is set so that just enough hydrogen is introduced so that the ongoing chemical reaction occupies the leafy crop canopy 38 and immediately adjacent area. The release point of the reagent is preferably directly below the leafy canopy 38 of the crop. For certain crops that do not benefit from direct exposure to a reagent such as hydrogen, the release point would then be directly above the leafy canopy 38. In this case the diluted hydrogen would not contact the crops as hydrogen rises above the air. The hydrogen then neutralizes the existing $NO_x$ and ozone in the local sphere. Furthermore, new $NO_x$ and $O_3$ that is moving into the leafy area by diffusion or dispersion across the chemical gradient created in the sphere by the initial neutralization is then neutralized.

Finally, the flow valve 24 can be electronically adjusted by an electronic controller 32. The electronic controller 32 receives data from sensors 34 A-D in the field. These sensors convey signals via wired or wireless means. The types of sensors relaying data to the reagent control unit include:

temperature sensors 34A, wind velocity anemometers 34B, photosynthetically active radiation level (PAR) sensors 34C, reagent concentration level sensors 34D, and pollutant concentration level sensors 34E. While the use of air quality sensors was expensive in the past, the 2010s saw a trend towards the development of cheaper air-quality sensors, making the final component of the system 10 affordable and beneficial.

While applications of reagent may take place 24/7, in the preferred embodiment the prescription rate is higher and matches the higher pollution levels associated with photochemical reaction during high sunlight, at which time the plants' stomata are at their most open state therein allowing the toxic O3 gas) to enter the interior leaf space where damage occurs from the air pollutants, and/or, rate of delivery can be adjusted to the dynamic ambient O3 by employing a real-time air pollutant metering device positioned in the leafy plant canopy 38.

Figure 2:
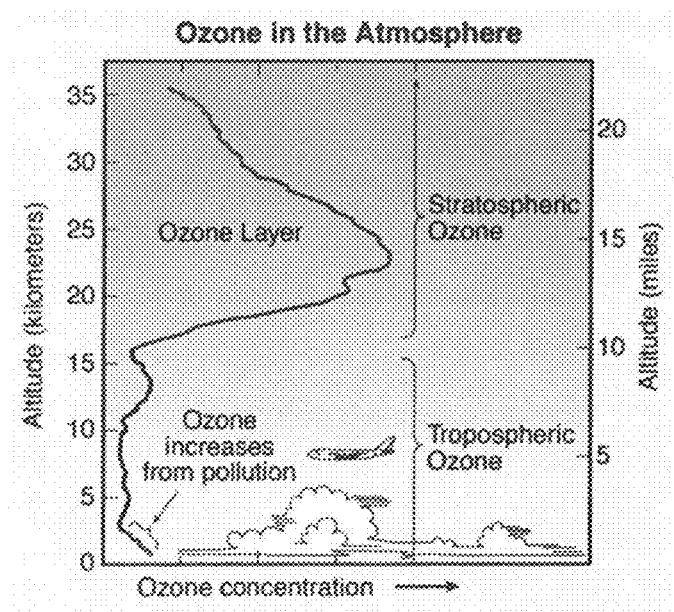
Figure 3:
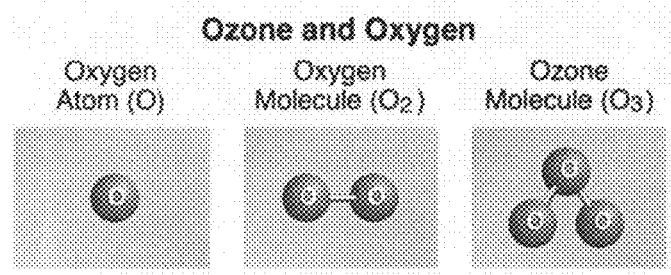
Figure 4:
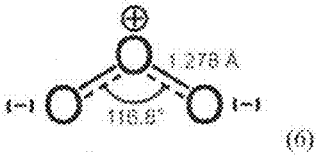

Referring to FIG. 2, there are two main areas in which Ozone collects and affects life on earth. The first resides in the stratosphere which begins at 16 kilometers and extends up to 50 kilometers from earth. This is where the ozone layer resides and hold great importance for life in filtering out the UV-B light emitted by the sun. The second area resides below 16 kilometers, within the troposphere. The tropospheric ozone is of interest because of its negative effects on the health of plants and animals. Concentrations of ozone between these two regions vary greatly with 90% of all ozone residing in the stratosphere, while only 10% resides in the troposphere. Concentration ranges within the stratosphere are 1000 ppb to 15,000 ppb. The troposphere averages ~75 ppb but can reach levels as high as 250 ppb; this value depends on weather and region.

Ozone production occurs in both regions of the atmosphere through different means. In the stratosphere, ozone is produced naturally though a photochemical reaction where UV-light (?<242 nm) strikes an oxygen molecule, splitting the pair into single oxygen atoms. The unpaired oxygens then react with other oxygen molecules thus producing ozone.

$$O_2+(e-, h\nu, T) \rightarrow 2O\ (O_2^*)\ \lambda<242\ \text{nm} \tag{1}$$

$$O_2+O+M \rightarrow O_3+M \tag{2}$$

$$O_2^*+O_2 \rightarrow O_3 \tag{3}$$

M is commonly O2 or N2; this stabilizes the products through collisions.

In the troposphere, the short wavelengths needed to produce oxygen atoms aren't present. Instead the production of ozone is facilitated by longer wavelengths and a variety of chemicals produced during industrial processes. CH4, CO, and non-methane volatile organic compounds (VOC) react in the presence of nitrogen oxides (NO$_x$) which act as catalysts. In the below reactions, 4-7 denote the reactions that would happen if ozone production occurred in urban areas, while 8-12 are reflective of non-urban environments.

$$R+O_2+M \rightarrow RO_2+M \tag{4}$$

$$RO_2+NO \rightarrow RO+NO_2 \tag{5}$$

$$NO_2+h\nu \rightarrow NO+O\ \lambda \leq 400\ \text{nm} \tag{6}$$

$$O+O_2+M \rightarrow O_3+M \tag{7}$$

R denotes radical species (Ex: H, CH$_3$, and CH$_3$C(O))

$$CO+OH \rightarrow H+CO_2 \tag{8}$$

$$H+O_2+M \rightarrow HO_2+M \tag{9}$$

$$HO_2+NO \rightarrow HO+NO_2 \tag{10}$$

$$NO_2+h\nu \rightarrow NO+O\ \lambda \leq 400\ \text{nm} \tag{11}$$

$$O+O_2+M \rightarrow O_3+M \tag{12}$$

Ozone's Effect on Plants:

Due to ozone's properties, in high enough concentrations it can be very detrimental to organic life. This is especially problematic for plants, with ozone accounting for 90% of the damage to plants in North America. Due to tropospheric ozone requiring sunlight to be produced, growing seasons coincide with increased levels of ozone. Ozone with a seasonal average of 60 ppb has led to crop yield reductions of 0.3-5.1% for corn, 5.3-24% for soybeans, 16-35% for cotton, and 0.9-51% for wheat. This damage occurs when the sunlight hitting the leaves causes the gas exchanging stomata to open. Ozone then enters the stomata, dissolves into the water within the intercellular spaces of the leaf and reacts with chemicals within the plant. Though the mode of action isn't known for certain, some observations have shown that cell membranes can become leaky slowing photosynthesis and thus plant growth. The reactants from ozone oxidation have also been shown to be detrimental to the mitochondria's energy production potential, reduction in fruit and flower numbers and the efficiency of water utilization. While not fully supported yet, it is believed that ozone could also impair the plants' resistance from bacteria, drought, fungi, insects, and viruses.

Figure 5:
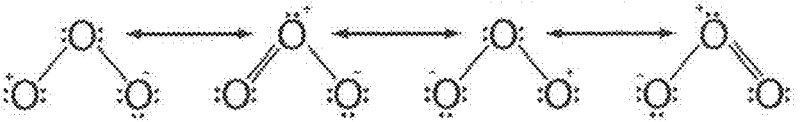

Chemical and Physical Properties of Ozone:

Ozone is the unstable triatomic allotropic modification of O$_2$. It carries very powerful oxidation properties making it very good at neutralizing organic compounds and oxidizing inorganic molecules to their highest oxidation states. Due to this, it is produced for chemical, industrial, and sanitary purposes. It is a pale blue gas at room temperature, in liquid phase it's an indigo-blue liquid, and as a solid it forms violet-black crystals. Referring to FIG. 5, ozone is resonance stabilized which is why there's resistance to decomposition at low temperatures. It has a positive standard molar enthalpy and Gibbs energy of formation, a positive molar entropy, and a positive molar heat capacity. This means that the formation of ozone is an endothermic process that is not spontaneous. Entropy increases due to the coalescence of an oxygen molecule and an oxygen atom. This means that ozone is unstable in this form and that the reverse reaction would be thermodynamically favorable.

Decomposition Strategies:

The decomposition of Ozone can be carried out through a variety of means but doing so effectively in an open-air environment limits those-which could be beneficial. Homogenous reactions will be the best option, heterogeneous will also be briefly discussed. The reactions need to occur at temperature ranges and pressures that are found at ground level ~70° F. (294.3° K), and pressure ~750 mmHg.

Homogeneous Reaction:

In homogeneous reactions, the ozone gas is subjected to another gas leading to its decomposition. This means would be the most relevant to current infrastructure, although it should be noted that separate delivery tubes might be advantageous to lessen reactions occurring between CO$_2$ and the candidates.

This method does however have drawbacks in the form of selectivity and occurrence of reactions due to dilutions. While this can be mitigated to some degree using Le Chatelier's principle, gases must remain within safe ranges for plants, workers, environments, and the like.

Common ozone depleting substances include:
chlorofluorocarbons (CFCs)
hydrochlorofluorocarbons (HCFCs)
hydrobromoflurocarbons (HBFCs)
halons
methyl bromide
carbon tetrachloride
methyl chloroform Rate expression: $k(T)=A\,(T/298\,K)^n\,e^{-E_a/RT}$
Second order: cm$^3$/molecule s Candidate(s) 1: NO, NO$_2$ $$O_3+NO\rightarrow NO_2+O_2$$

$$O_3+NO_2\rightarrow NO_3+O_2$$

$$NO_3+NO_2\leftarrow\rightarrow N_2O_5$$

NO (nitric oxide) and NO$_2$ (nitrogen dioxide) serve as good candidates due to their ability to react with ozone at a rate that is only surpassed by the radical candidates in FIG. 7. NO and NO$_2$ have also been shown to act as a phytohormone for a range of plants and will accumulate in the plant when there is oxidative stress. With proper amounts of soil nitrogen, exposing plants to gaseous NO and NO$_2$ has resulted in an increase in nutrient uptake, photosynthesis, and nutrient metabolism. Associated exposure levels are in the range from 10-250 ppb, which is also within concentration ranges of O$_3$. If volatile organic compounds (VOCs) are present in high enough concentrations, O$_3$ production can occur. However, the rate at which this happens is much slower and would likely occur at a large distance from the plants.

Candidate 2:

$$CH_4+O_3\rightarrow CO+CO_2+CH_2O_2$$

CH$_4$ commonly referred to as methane, is another gaseous candidate to consider. While there isn't much literature on its interaction with O$_3$, it does appear to react. While this rate is slowest of all the candidates, it occurs naturally in soil and the products aren't formed at levels that would be toxic to plants. As far as the effects it has on plant growth, some studies have shown an increase in dry shoot weight of maize and possible increase in root biomass in rice patties.

Candidate 3:

$$6\,PH_3+8\,O_3\rightarrow 3\,P_2O_5+9\,H_2O$$

Another candidate to consider would be PH$_3$ (Phosphine). It's reaction with ozone at high concentrations leads to an immediate explosion, but with dilutions of CO$_2$ or other gases this can be mitigated. Currently it is used as a fumigant in agriculture and grain storage with the gaseous methods being the fastest and most effective. While it is a possible candidate, there are drawbacks in that it is toxic to humans above an 8-hour average with a concentration of 300 ppb. Secondary uses of this gas could be to treat pests, although pest resistance has been found to occur in some cases.

Candidate 4:

$$SO_2+O_3\rightarrow SO_3+O_2$$

SO$_2$ (sulfur dioxide) would not be a good candidate for this application. While SO$_2$ does react with O$_3$, it does so at a very slow rate. To add to this assessment, SO$_2$ gas given to plants with NO$_2$ present effectively stopped the plants from responding to NO$_2$, preventing the plants from detoxifying properly.

This resulted in negative growth effects in the plants.

Candidate 5:

$$2\,NH_3+4\,O_3\rightarrow O_2+H_2O+NH_4NO_3$$

The 5$^{th}$ candidate: NH$_3$ (Ammonia) appears to be much like nitric oxides in that they both provide a nitrogen source for the plant. Ammonia in liquid and solid form (salts) is already used as fertilizer for many plants, so its safety isn't of concern. Gaseous ammonia was found to not negatively affect photosynthesis, and possibly increase CO$_2$ uptake and stomatal conductance. These factors greatly help drought sensitivity. While this offers a potential candidate for ozone removal and secondary benefits as aiding in plant growth, NH$_3$ does react with CO$_2$. As both would be administered as gasses, and the concentrations low, the reaction shouldn't occur to a large degree.

Candidate 6:

$$CO+O_3\rightarrow CO_2+O_2$$

The final non-radical gaseous candidate is CO (carbon monoxide). The decomposition of ozone occurs slowly in a pure/isolated system, but upon introduction of certain impurities, the rate of reaction is much faster until the impurity is consumed. Louis et al. believe this impurity to be methane, a gas found in the atmosphere at concentrations of 1500 ppb. Methane is produced during anaerobic digestion of organic waste which occurs primarily in wetlands. If atmospheric methane doesn't provide enough of a catalyst, the use of auxiliary methane might be required to provide the reaction with enough speed to warrant use. In plants, CO has been found to be very important for plant signaling. Exogenous CO in low concentrations has been shown to have positive effects and offer resistance from a variety of stressors, making CO a viable candidate.

Radical/Diradical Candidate(s):

$$O_3+O\cdot\rightarrow O_2+O_2$$

$$O_3+H\cdot\rightarrow\cdot OH+O_2$$

$$O_3+N\rightarrow O_2+NO$$

While the radicals/diradicals candidates do react with ozone to a great degree, their reactive nature lessens their selectivity. This means that production of the radical would likely have to occur at the very end of the distribution system, making this means of ozone depletion not very viable in terms of cost and effective targeting of ozone.

Homogeneous Candidate Discussion:

While all the homogeneous reactions shown above offer promise in ozone depletion, speed of the reaction, effective delivery, secondary uses, and toxicity to plants are all things that should be considered. The best candidates to pursue further testing based off the compilation of literature would be: NO, NO$_2$, NH$_3$, CO/CH$_4$ mixture, PH$_3$/CO$_2$ mixture, and CH$_4$ from most desirable to least desirable, respectively.

NO is especially advantageous since it reacts with ozone well, has a secondary benefit of aiding in plant growth/development, and produces the product NO$_2$. NO$_2$ also decomposes ozone, to a lesser degree compared to its reduced form, but still provides well known benefits to some plants. NH$_3$ reactivity to ozone, coupled with its nitrogen providing benefits to plants, make it the next most viable candidate. One drawback is that it will react with CO$_2$ to some degree. The next candidate would likely need to be a mixture of CO and $CH_4$. This is due to $CH_4$ helping with the ozone decomposition reaction. Literature also suggests that CO can have positive effects on maintaining plant homeostasis.

A $PH_3/CO_2$ mixture is another option to consider. It is already used in agricultural applications as a fumigant for pests, which offers an advantage that isn't seen in the other candidates. Considerations for this gas are its volatile nature and ability to combust in air at high enough concentrations, problems which a mixture would alleviate. The last gaseous candidate to consider, $CH_4$, appears to react with ozone to the slowest degree of any of the others. While this isn't ideal, $CH_4$ is naturally found in soil and might provide some benefit to plant growth. The only candidates that don't seem viable are $SO_2$ due to its lagging reaction time and negative effects to plant growth. Radicals and diradicals also don't seem like a good option due to their high reactivity and production.

Heterogeneous Reaction:

In this reaction there are two means by which it can occur, the first is the use of a solid and the second is the use of a liquid. For the first, metals/metal oxides (noble metals and oxides of transition metals) can be impregnated on a variety of substrates. Air is then passed though said substrate and the ozone is removed to varying degrees depending on a variety of factors. This method is often used in industry to clean air being exhausted into the atmosphere.

In the liquid-gas reaction, $H_2O$ high in pH is typically used due to its ease of availability as well as serving as a —OH supplier which decomposes ozone. A variety of compounds can be added to the water to increase its ability to scavenge —OH radicals, further increasing the rate of the reactions such as bicarbonate and organic compounds. As heterogeneous ozone decomposition relations are the primary reaction type used in industries and labs, there is a lot of information that could be expanded on if there is further interest in using this. However, this would be mostly beneficial in an enclosed environment.

Ozone is a very reactive molecule that both benefits and hurts life on earth depending on proximity. Tropospheric ozone is an issue that is seen around the world and can be caused by many different factors. While it effects organisms to different extents, mankind's reliance on increased agriculture output is an important task going forward. Homogeneous and heterogeneous reactions each offer different benefits. Homogeneous (gas-gas) reactions would allow the most plausible benefit to open canopies while also offering secondary benefits depending on the gas chosen. Heterogeneous reactions would offer a much greater rate of ozone decomposition but would be more applicable to indoor or closed canopy growing operations.

The descriptions above and the accompanying materials should be interpreted in the illustrative and not the limited sense. While the invention has been disclosed in connection with the preferred embodiment or embodiments thereof, it should be understood that there may be other embodiments which fall within the scope of the invention.

The invention claimed is:

1. A. method for enhancing plant crop growth, comprising the steps of:

a. providing a supply of H2 gas reagent;
b. filtering impurities from the reagent;
c. compressing the reagent;
d. storing the compressed reagent in a tank;
e. diluting the compressed reagent to at or below 4% concentration;
f. regulating the reagent pressure;
g. controlling a rate of flow of the compressed reagent using a valve connected to the tank; and
h. applying the reagent to the plant crop, whereby the reagent is used to neutralize air pollutants.

2. The method of claim 1, wherein a source of the reagent is electrolysis.

3. The method of claim 1, wherein a source of the readent is a steam methane reformer.

4. The method of claim 1, wherein the filtration step is accomplished using an electrochemical purification system.

5. The method of claim 4, wherein the electrochemical purification system is communicatively connected to a reagent source via a hose.

6. The method of claim 1, wherein the step of comprising the reagent is accomplished by an electrochemical hydrogen compressor.

7. The method of claim 6, wherein the electrochemical hydrogen compressor is communicatively connected to a filtration device via a hose.

8. The method of claim 7, wherein the reagent storage tank is communicatively connected to the electrochemical hydrogen compressor via a hose.

9. The method of claim 1, wherein the reagent is diluted using a venturi valve.

10. The method of claim 9, wherein the venturi valve is communicatively coupled to the tank via a hose.

11. The method of claim 1, wherein the step of regulation reagent pressure is accomplished by a regulator communicatively coupled to a dilution mechanism via a hose.

12. The method of claim 11, wherein the pressure regulator is a single-stage or double-stage regulator.

13. The method of claim 11, wherein the flow control valve is communicatively coupled to a piping distribution array via a layflat manifold and which is communicatively coupled to the pressure regulator via a hose.

14. The method of claim 1, wherein the step of regulating reagent pressure is accomplished by a control unit communicatively coupled to the flow control valve and sensors, communicatively connected to the control unit, embedded in the field.

15. The methods of claim 1, wherein a rate of application of the reagent is determined by the level of air pollution, so that a chemical neutralizing effect envelopes, but does not exceed, the space occupied by the crops' canopy.

* * * * *